United States Patent [19]

Bellamy et al.

[11] Patent Number: 5,561,154
[45] Date of Patent: Oct. 1, 1996

[54] TREATMENT OF ACUTE URINARY RETENTION

[75] Inventors: François Bellamy, Saulon la Rue; Philippe Reginault, Fontaine lès Dijon; Bernard Rasquin, Nogent sur Marne, all of France

[73] Assignee: Institut de Recherches Chimiques et Bioloques Appliquees IRCEBA, France

[21] Appl. No.: 391,233

[22] Filed: Feb. 21, 1995

Related U.S. Application Data

[63] Continuation-in-part of Ser. No. 281,425, Jul. 27, 1994, Pat. No. 5,451,609.

[51] Int. Cl.$^6$ .......................... A61K 31/135; A61K 31/21
[52] U.S. Cl. ............................................................ 514/546
[58] Field of Search ................................................ 514/546

[56] References Cited

U.S. PATENT DOCUMENTS 5,182,270  1/1993  Musson et al. ........................... 514/58

OTHER PUBLICATIONS

Vidal 1993 (dictionary), 69th Edition, Editions du Vidal, Paris 1993, pp. 239, 689 and 1489–1490.

"In Vitro and In Vivo α–Blocking Activity of Thymoxamine and Its Two Metabolites", M. H. Creuzet, et al., J. Pharm. Pharmacol. 1980, vol. 32, pp. 209–213.

"$\alpha_1$–and $\alpha_2$–Adrenoceptor Selectivity of Moxisylyte (Thymoxamine) and Its Metabolites in the Pithed Rat", J. Roquebert, et al., Arch. Int. Pharmacodyn, 1983, vol. 266, pp. 282–293.

Poirier et al., J. Urol. (Baltimore) (1988), 140(1), 165–7.

Primary Examiner—Phyllis G. Spivack
Attorney, Agent, or Firm—Ostrolenk, Faber, Gerb & Soffen, LLP

[57] ABSTRACT

This invention is concerned with a composition and method for the treatment of acute urinary retention, whereby deacetyl moxisylyte or one of its non-toxic salts is administered in a ready to use aqueous solution by the intravenous route to induce a decrease in the urethral contractility.

15 Claims, No Drawings

TREATMENT OF ACUTE URINARY RETENTION

CROSS REFERENCE

This invention is a continuation-in-part of a previous U.S. patent application Ser. No. 08/281,425 filed on Jul. 27, 1994 and now U.S. Pat. No. 5,451,609.

FIELD OF THE INVENTION

Acute urinary retention can often occur after any surgical operation. This invention relates to a technique to combat acute urinary retention and to be precise, is concerned with (i) a novel therapeutical composition and (ii) a novel method for the treatment of acute urinary retention involving both the use of deacetyl moxisylyte or a non-toxic salt thereof as a drug which induces a decrease in the urethra contractility by intravenous route.

The previous U.S. patent application dealt with a treatment of impotence using deacetyl moxisylyte or one of its non-toxic salts as a drug inducing a substantially rigid penile erection by intracavernosal injection. This invention discloses the use of the very same deacetyl moxisylyte and non-toxic salts thereof for treating per i.v. route acute urinary retention.

PRIOR ART

Moxisylyte (also called thymoxamine), which is a known α-adrenergic blocking agent, cited in particular in *The Merck Index*, 11th edition, 1989, page 991 (monograph number: 6204), corresponds to the systematic nomenclature of 4-[2-(dimethylamino)ethoxy]-2-methyl-5-(1methylethyl)phenol acetate and has the following structure:

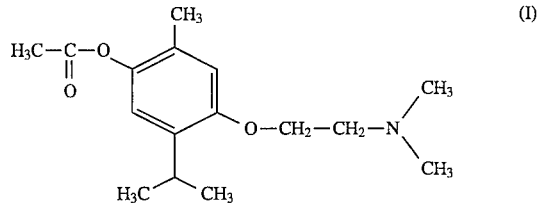

The following moxisylyte-containing specialties were commercialized, in particular in France, in view of the α-adrenergic blocking activities of the moxisylyte compound:

- tablets each containing 120 mg of moxisylyte.HCl for treating (in general with 4 tablets per day) benign hypertrophy of the prostate gland (i.e. prostatic adenoma) and its functional manifestations, see the VIDAL®1993 dictionnary, 69th edition, Editions du Vidal, Paris 1993, pages 1489–1490 (entry: "UROALPHA"),
- tablets each containing 30 mg of moxisylyte.HCl for treating (in general with 1–2 tablets per day) peripheral artery diseases of ederly persons, see the very same VIDAL®1993 dictionnary, page 239 (entry: "CARLYTENE 30 mg"), and injectable preparations each containing 10 mg or 20 mg of moxisylyte.HCl wherein the moxisylyte compound intervenes as a drug inducing a substantially rigid penile erection by intracavernosal injection, see the very same VIDAL®1993 dictionnary, page 689 (entries: "ICAVEX 10 mg" and "ICAVEX 20 mg).

The α-adrenergic blocking activities of moxisylyte and its two metabolites are disclosed as well as their antihypertensive effects in the articles by M. H. CREUZET et al., *J. Pharm. Pharmacol.*, 32, pages 209–213, (1980) and J. ROQUEBERT et al., *Arch. Int. Pharmacodyn.*, 266, pages 282–293 (1983).

Moxisylyte has the drawbacks of being (i) unstable in water solutions and (ii) dose dependent hepatotoxic peroral route (i.e. more than 480 mg/day). Taking into account that hepatotoxicity, moxisylyte in tablet form has been severely criticized. The French health authorities withdrew the UROALPHA specialty in from the market in 1994.

As indicated in the parent application, aqueous solutions of moxisylyte are not stable at room temperature. Moxisylyte, which comprises in its structure an acetate moiety, is hydrolyzed by bases to give a phenol compound, and by acids to give a quinone compound after oxidation.

Consequently, it is not possible to commercialize moxisylyte in the form of a ready to use injectable aqueous solution.

As commercialized in France (see the above cited VIDAL®1993), the moxisylyte.HCl compound of the ICAVEX 10 mg and ICAVEX 20 mg specialties is in the form of a lyophilized product. It is provided as a syringe containing the lyophilized moxisylyte.HCl powder, an ampoule containing water as a solvent and a needle destined to equip said syringe. The user fills the syringe with the solvent in order to dissolve the lyophilized moxisylyte.HCl powder before injecting the resulting solution by the intracavernosal route.

After oral or parenteral administration, moxisylyte is deacetylated by plasmatic esterases, and at the plasma level are found two metabolites: (a) deacetyl moxisylyte (in short: DAM), which corresponds to the systematic nomenclature of 4-[2-(dimethylamino)ethoxy]-2-methyl-5-(1-methylethyl)phenol and has the following structure:

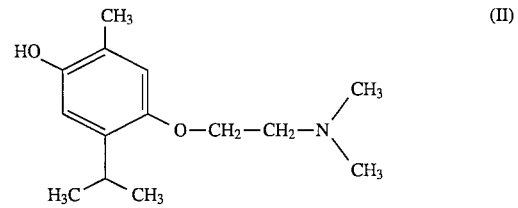

as a major or main metabolite (in both the free and conjugated forms), and (b) N-monodemethyl deacetyl moxisylyte (in short MDAM), which corresponds to the systematic nomenclature of 4-[2-(methylamino)ethoxy]-2-methyl-5-(1-methylethyl)phenol and has the following structure:

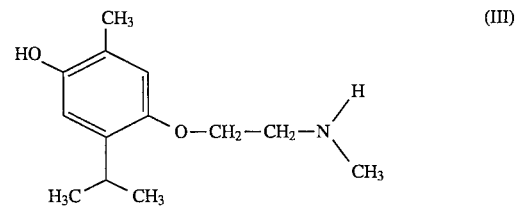

as a minor or secondary metabolite (in the conjugated form).

The above conjugate form of DAM and MDAM is a glucuro and/or a sulfo one.

U.S. Pat. No. 5,182,270 (to Donald G. MUSSON et al.) provides a stable moxisylyte solution, in which dimethyl-beta-cyclodextrin is a stabilizing agent for preventing moxisylyte (used here as an α-adrenergic blocking agent) from being hydrolyzed. When said dimethyl-beta-cyclodextrin is used as a stabilizing agent, a pH 5 solution containing 1 mg/ml of moxisylyte is stable at 45° C. for 3 months.

However such a dimethyl-beta-cyclodextrin/moxisylyte formulation has the drawback of being very expensive, because the price of dimethyl-beta-cyclodextrin is high. Moreover injecting said dimethyl-beta-cyclodextrin/moxisylyte formulation by the parenteral route would mean injecting a stabilizing product, which has an unknown long term toxicity and which does not provide per se any therapeutical advantage.

On the other hand the parent application provides impotent male patients with an aqueous solution of deacetyl moxisylyte, which is stable, for inducing a substantially rigid penile erection by intracavernosal injection.

SUMMARY OF THE INVENTION

It has been surprisingly found now that deacetyl moxisylyte, a product known per se in particular as a metabolite of moxisylyte, which is stable in aqueous solution, unlike moxisylyte, is (i) active as an urethral relaxant agent in the treatment of acute urinary retention, and (ii) substantially devoid of hepatotoxicity when administered iv at 50 mg or less doses.

Consequently, a novel therapeutic composition is provided and a novel method of treatment of acute urinary retention using deacetyl moxisylyte or one of its non-toxic salts as a drug to induce a decrease in the urethra contractility or contraction administered by the i.v. route.

SUBJECT OF THE INVENTION

According to a first aspect of the invention, a composition to combat acute urinary retention is provided, said composition comprising in a ready to use aqueous solution of a therapeutically effective amount of a compound inducing a decrease in the urethra contractility which is selected from the group consisting of (i) deacetyl moxisylyte, and (ii) non-toxic salts thereof, said aqueous solution to be administered by i.v. route.

According to a second aspect of the invention, a method for the treatment of acute urinary retention is provided, said method comprising administering, by intravenous injection, to a patient in need of such a treatment, an aqueous solution containing a therapeutically effective amount of a compound selected from the group consisting of (i) deacetyl moxisylyte, and (ii) non-toxic salts thereof, as an urethral relaxant agent.

DETAILED DISCLOSURE OF THE INVENTION

The composition to combat acute urinary retention according to the invention presents the advantage to be simple and economical to use. The active ingredient, which induces the decrease in the urethra contractility, namely deacetyl moxisylyte (DAM) of the formula II or one of its non-toxic salts, is dissolved in an aqueous solution for i.v. injection according to classical well known technique.

Among the non-toxic salts of deacetyl moxisylyte are included here the physiologically acceptable acid addition salts, in particular those obtained by reacting the deacetyl moxisylyte free base with an inorganic or organic acid, such as hydrochloric acid or tartaric acid.

The composition to combat acute urinary retention according to the invention, which is made from pure (i.e. distilled, bidistilled or preferably deionized) water and from DAM or one of its non-toxic salts as an urethral relaxant agent, can contain further excipient products. Advantageously, said excipient products can comprise:

(a) a buffer material, (b) an antioxidant material, and/or (c) an organic co-solvent.

According to the invention, in cases where it is necessary to adjust the pH of the DAM-containing aqueous solution, it is recommended to use a solution buffered at pH 5–7 with potassium dihydrogen phosphate ($KH_2PO_4$), sodium dihydrogen phosphate ($NaH_2PO_4$), disodium hydrogen phosphate ($Na_2HPO_4$), sodium chloride (NaCl), sodium hydroxide (NaOH) or mixtures thereof. In those cases, the buffer material (here $KH_2PO_4$, $NaH_2PO_4$, $Na_2HPO_4$, NaCl, NaOH or a mixture thereof) will be at a concentration of from 2 to 15 g/l (i.e. 0.2–1.5% p/v) and preferably at a concentration of from 8 to 12 g/l (i.e. 0.8–1.2% p/v).

According to the invention, in cases where it is advantageous to add an antioxidant material into the DAM-containing aqueous solution, it is prefered to use a DAM-containing solution which comprises from 0.001 to 0.01 g/l (i.e. 0.01–0.1% p/v) of an antioxidant agent such as for instance $K_2SO_3$ or (preferably) $Na_2SO_3$, $KHSO_3$ or (preferably) $NaHSO_3$, $K_2S_2O_5$ or (preferably) $Na_2S_2O_5$, or ascorbic acid or a physiologically acceptable salt thereof.

The addition of an antioxidant material can be either replaced by or associated with a preparation technique wherein the aqueous composition according to the invention is prepared from its components under an inert atmosphere (in particular under nitrogen or argon), whereby the solvent (or solvents) used is (are) previously degassed.

According to the invention, it is also possible to add into the DAM-containing aqueous solution a supplemental solvent which is used here as a co-solvent. That co-solvent is in a general manner an alcohol or polyol compound. In the case where such a co-solvent is present, it is preferred to use ethanol, propylene glycol, glycerol or a polyethylene glycol, (such as $PEG_{300}$ or $PEG_{400}$) in a proportion up to 50% by volume with respect to the total volume of the composition to combat acute urinary retention of the invention.

In the parent application it was pointed out that DAM, the active ingredient, is effectively soluble and stable in water in the form of its hydrochloride salt. Deacetyl moxisylyte hydrochloride (DAM.HCl) is soluble up to a concentration of 10% p/v, which is the upper therapeutically acceptable concentration, in pure (i.e. distilled, bidistilled or preferably deionized) water and in aqueous solutions buffered at pH 5–7. Water solutions containing 1% p/v of deacetyl moxisylyte hydrochloride without any antioxidant and kept at pH 5, 6 and 7, are stable for 15 days at 25° C. and for 90 minutes at 121° C. Identical solutions, in which $Na_2SO_3$ used as an antioxidant is added in order to reach a sodium sulfite concentration of 0.1 p/v in said solutions, do not give any coloration and are stable for 15 days at 95° C. More details regarding the solubility and stability in water of DAM.HCl are given in the parent application.

The DAM-containing aqueous solution of this invention can be sterilized according to a well known classical technique without degradation of DAM. Autoclave sterilization for 15 minutes at 121° C. and sterilizing filtration are here the preferred sterilization techniques.

In a general manner, said DAM-containing aqueous solution will preferably contain from 0.5 to 7.5% p/v of DAM or one of its non-toxic salts.

The vesical neck and the proximal urethra are rich in α-adrenergic receptors and they are under the dependence of the noradrenergic system. Surgery (in general) and anesthetic agents (in particular) can modify or affect the functions of these organs.

For instance, anticholinergic anesthetics can depress the detrusor contractility. Chirurgical stress can induce an increase in the urethral tonus, thus increasing the vesical orifice resistance.

DAM and its non-toxic salts when administered by the i.v. route cause an increase in the vesical orifice and thus induce a decrease in the urinary outflow resistance. In other words, DAM and its non-toxic salts are helping by the i.v. route to empty the bladder and to make micturition easy.

The acute urinary retention, which is treated according to this invention, can have several origins, namely a neurogenic origin, a postoperative origin, an urological origin, a psycho-behavioral origin or can be idiopathic. The most frequent acute urinary retention is the postoperative one.

On the other hand, DAM and its non-toxic salts do not act on every chronic urinary retention. The reduction in urinary outflow resistance that they can induce, is not statistically significant in all cases where chronic urinary retentions are concerned.

To combat the acute urinary retention, what is important in this invention, is to block a portion of the $\alpha_1$-adrenergic receptors which control the ability of the urethra to maintain contraction for reducing said ability in order to allow micturition.

BEST MODE

The best mode for carrying out the invention consists in administering by intravenous injection, to a patient in need of a treatment to combat acute urinary retention, a single daily dose of from 5 to 50 mg of deacetyl moxisylyte or one of its non-toxic acid addition salts. The recommended posology is one injection per day for 1–3 weeks. The prefered active ingredient is the DAM.HCl salt.

Further characteristics and advantages of the invention will be understood more clearly from the following description of preparatory Examples and pharmacological assays, which in no way imply a limitation and are given by way of illustration.

EXAMPLES 1–6

Compositions A–F according to the invention were prepared according to the formulations presented in Table I hereinafter. From those compositions Ex 1–Ex 6 were obtained as follows:
Ex 1: 1 ml of A (DAM.HCl amount: 10 mg),
Ex 2: 1 ml of B (DAM.HCl amount: 10 mg),
Ex 3: 1 ml of C (DAM.HCl amount: 20 mg),
Ex 4: 1 ml of D (DAM.HCl amount: 35 mg),
Ex 5: 5 ml of E (DAM.HCl amount: 50 mg),
Ex 6: 0.5 ml of F+9.5 ml of $H_2O$ (DAM.HCl amount: 5 mg).

Syringes, destined for injecting (per a single injection) a volume of from 1 to 10 ml of liquid, were filled with these example preparations so as to be ready to use and contained each from 5 to 50 mg of deacetyl moxisylyte hydrochloride (DAM.HCl).

TABLE I

| | Formulations of compositions A–F | | | | | |
|---|---|---|---|---|---|---|
| | A | B | C | D | E | F |
| DAM.HCl | 1 g | 1 g | 2 g | 3.5 g | 1 g | 1 g |
| NaCl | 0.2 g | 0.2 g | — | — | — | — |
| $KH_2PO_4$ | 0.8 g | 0.4 g | 0.4 g | 0.4 g | 0.8 g | 0.8 g |
| $NaH_2PO_4$ | 0.1 g | 0.6 g | 0.6 g | 0.6 g | 0.1 g | 0.1 g |
| $Na_2SO_3$ | 0.01 g | — | — | — | — | — |
| Ascorbic acid | — | 0.05 g | 0.05 g | — | — | — |
| Propylene glycol | — | — | — | 30 g | — | — |
| Ethanol | — | — | — | — | 20 g | — |
| $PEG_{300}$ | — | — | — | — | — | 40 g |
| $H_2O$ up to | 100 ml | 100 ml | 100 ml | 100 ml | 100 ml | 100 ml |

Pharmalogical Assays In Vitro

1. Assays On Isolated Rabbit Urethra

After slaughtering of male rabbits, each urethra was taken out then placed into a receptacle containing a physiological saline aqueous solution, and kept at 37° C. with an oxygen/carbon oxide mixture (95/5 p/p). One end of the urethra was fixed to a pressure captor linked to a recording device for measuring the organ contractions.

Contracturing effects of noradrenaline were determined by succesive infusions of increasing contractions up to the contraction corresponding to the maximal amplitude. The measures were carded out with and without DAM.HCl.

The activity of DAM.HCl was measured as a $pA_2$ value, $pA_2$ being here the cologarithm of the antagonist molar concentration in the presence of which the noradrenaline concentration needs to be multiplied by two to obtain the same effect in the absence of antagonist.

$pA_2$ of DAM.HCl=8.5+0.25 (5 experiments)

On isolated rabbit urethra, DAM.HCl inhibits the contraction induced by noradrenaline used here as an α-adrenergic agonist.

2. Study With Radioactive Ligands

α-adrenoreceptors can be by use of a $^3H$- or $_{125}I$- labelled specific antagonist (or agonist) on membrane preparations of the concerned organ, here rabbit urethra.

A male rabbit urethral grinding was filtered then centrifugated. The filtrate thus obtained is a membrane preparation which was incubated with a radioactive ligand, namely ($^{125}I$)-HEAT [wherein HEAT is 2-[2-(3-iodio-4-hydroxyphenyl)ethyl-aminoethyl]-tetralone for the $\alpha_1$-adrenoreceptors, and ($^3H$)-rauwolscine for the $\alpha_2$-adrenoreceptors.

The incubations were carded out in the absence or in the presence of an increasing concentration of the product to be tested. The affinity was measured by means of the inhibition coefficient (Ki). The results are given in table II.

TABLE II

|  | $\alpha_1$-adrenoreceptors | $\alpha_2$-adrenoreceptors |
| --- | --- | --- |
| Ki (nM) | 109 ± 20 | 637 ± 94 |

On male rabbit urethral membrane fractions, DAM.HCl inhibits competitively and specifically the binding of specific agonists to $\alpha_1$- and $\alpha_2$-adrenoreceptors. From the results thus obtained, it is seen that DAM.HCl is six times more active on $\alpha_1$-adrenoreceptors than on $\alpha_2$-adrenoreceptors.

Pharmacological Assays In Vivo

3. Study On Anesthetized Rabbits

Male White New-Zealand rabbits (weighing 3 kg each) were anesthetized with ethyl-urethane. Arterial pressure (AP) was measured with a pressure captor linked to a catheter located in the carotid; urethral pressure (UP) was determined with a pressure captor linked to a catheter introduced into the urethra and located at the level of the vesical base. The femoral vein was also catheterized for administering the products to be tested.

The increases in the urethral and arterial pressures, which were induced by noradrenaline, were determined after i.v. injections of increasing doses for periods of 3 minutes each, from 15 minutes before the injection of the $\alpha$-blocking product to be tested to 15 minutes after said injection.

The results thus obtained are expressed hereinafter an inhibiting dose 50% (ID-50) which is defined as the dose of a-blocking product in the presence of which, the effect of the largest dose of noradrenaline is divided by a factor 2. See table III.

TABLE III

| ID-50 fo DAM.HCl (n = 5) | |
| --- | --- |
|  | ID-50 i.v. (mg/kg) |
| AP | 3.50 ± 0.65 |
| UP | 0.40 ± 0.03 |

DAM.HCl, in view of those results, is 8 or 9 times more active on UP than on AP and thus can be said uroselective.

4. Assays On Dogs

Adult male Beagle dogs were anesthetized by i.v. injection of sodium barbital (30 mg/kg).

The cannulation of each carotid and urethra allowed measurement of AP and UP. By derivation of the AP signal, the heart rate (HR) was recorded.

The increase in UP was induced by electric stimulation of the hypogastric nerve distal roots (10 ms, 30 Hz, 5s, 6–10 V). That increase in UP is determined before and 15 minutes after the injection of the $\alpha$-blocking agent to be tested.

The results were expressed by calculating a ID-50 defined as the dose of $\alpha$-blocking agent which inhibits 50% of the effects of the hypogastric nerve stimulation on UP. The effects of said ID-50 were determined on AP and HR in order to obtain a variation percentage with respect to the initial values. See table IV.

TABLE IV

| Effect of ID-50 of DAM.HCl on UP, AP and HR | | |
| --- | --- | --- |
| Effect on | Effect on | |
| UP | AP | HR |
| 0.05 ± 0.01 | –6% | –5% |

The stimulation of the hypogastric nerve releases the endogenous noradrenaline, which by activating $\alpha$-adrenergic receptors induces a contraction of the urethra smooth musculature, and consequently induces an increase in UP. Here, the DAM.HCl product opposes the effects of the hypogastric nerve stimulation and inhibits the increase in UP.

5. Absence of Hepatotoxicity

Adult male Wistar rats were daily injected with 1.5 mg/kg of DAM.HCl in saline solution (i.e. the solution of Ex 1) per i.v. route for 2 months, then slaughtered. The study of organs, in particular the analysis of the liver, showed no sign of hepatotoxicity.

What is claimed is:

1. A composition to combat acute urinary retention comprising an intravenously administrable, ready to use, aqueous solution of a therapeutically effective amount of a compound capable of inducing a decrease in the urethral contractility which is selected from the group consisting of
   (i) deacetyl moxisylyte, and
   (ii) non-toxic salts thereof.

2. A composition according to claim 1, containing from 0.5 to 7.5% p/v of deacetyl moxisylyte or one of its non-toxic acid addition salts.

3. A composition according to claim 1, having a pH between 5 and 7.

4. A composition according to claim 1, said composition further comprising from 0.01 to 0.1% p/v of an antioxidant material.

5. A composition according to claim 1, said composition further comprising an organic co-solvent representing up to 50% by volume with respect to the total volume of the composition.

6. A composition according to claim 5, wherein said co-solvent is selected from the group consisting of ethanol, propylene glycol, glycerol and polyethylene glycol.

7. A composition according to claim 5, containing 0.5 to 7.5% p/v of said compound, having a pH between 5 and 7 and containing 0.01 to 0.1% p/v of an antioxidant material.

8. A method for the treatment of acute urinary retention comprising administering, by intravenous injection, to a patient in need of said treatment, an aqueous solution containing a therapeutically effective amount of an urethral relaxant agent selected from the group consisting of
   (i) deacetyi moxisylyte, and
   (ii) non-toxic salts thereof.

9. A method according to claim 8, wherein the urethral relaxant agent is deacetyl moxisylyte hydrochloride.

10. A method according to claim 8 in which the aqueous solution has a pH between 5 and 7.

11. A method according to claim 8 in which the aqueous solution contains 0.01 to 0.1% p/v of an antioxidant material.

12. A method according to claim 8 in which the aqueous solution contains an organic co-solvent representing up to 50% by volume with respect to the total volume of the aqueous solution.

13. A method according to claim 12 in which the co-solvent is selected from the group consisting of ethanol, propylene glycol, glycerol and polyethylene glycol.

14. A method according to claim 13 in which the aqueous solution has a pH between 5 and 7 and contains 0.01 to 0.1% p/v of an antioxidant material.

15. A method according to claim 8 in which 0.5 to 7.5% p/v of said urethral relaxant agent is administered.

* * * * *